United States Patent
Yoshimitsu et al.

(10) Patent No.: US 10,918,577 B2
(45) Date of Patent: *Feb. 16, 2021

(54) DENTAL TREATMENT MATERIAL AND DENTAL TREATMENT MATERIAL KIT

(71) Applicant: GC Corporation, Shizuoka (JP)

(72) Inventors: Ryosuke Yoshimitsu, Tokyo (JP); Satomi Tateiwa, Tokyo (JP); Katsushi Yamamoto, Tokyo (JP); Syouichi Fukushima, Tokyo (JP)

(73) Assignee: GC Corporation, Shizuoka (JP)

( * ) Notice: Subject to any disclaimer, the term of this patent is extended or adjusted under 35 U.S.C. 154(b) by 65 days.

This patent is subject to a terminal disclaimer.

(21) Appl. No.: 16/303,936

(22) PCT Filed: Jun. 5, 2017

(86) PCT No.: PCT/JP2017/020896
§ 371 (c)(1),
(2) Date: Nov. 21, 2018

(87) PCT Pub. No.: WO2018/003419
PCT Pub. Date: Jan. 4, 2018

(65) Prior Publication Data
US 2020/0121563 A1 Apr. 23, 2020

(30) Foreign Application Priority Data

Jun. 30, 2016 (JP) ................................ 2016-131018

(51) Int. Cl.
| | |
|---|---|
| *A61K 6/20* | (2020.01) |
| *C03C 8/06* | (2006.01) |
| *C03C 8/08* | (2006.01) |
| *C03C 3/062* | (2006.01) |
| *C03C 4/00* | (2006.01) |
| *C03C 8/24* | (2006.01) |
| *A61C 19/08* | (2006.01) |

(52) U.S. Cl.
CPC ............... *A61K 6/20* (2020.01); *C03C 3/062* (2013.01); *C03C 4/0021* (2013.01); *C03C 8/06* (2013.01); *C03C 8/08* (2013.01); *C03C 8/24* (2013.01); *A61C 19/08* (2013.01); *C03C 2204/00* (2013.01); *C03C 2205/06* (2013.01)

(58) Field of Classification Search
CPC ...................................................... A61K 6/20
See application file for complete search history.

(56) References Cited

U.S. PATENT DOCUMENTS

| | | | |
|---|---|---|---|
| 4,209,434 A | 6/1980 | Wilson et al. | |
| 4,772,325 A | 9/1988 | Kwan et al. | |
| 4,775,592 A | 10/1988 | Akahane et al. | |
| 4,900,697 A | 2/1990 | Akahane et al. | |
| 5,032,445 A | 7/1991 | Scantlebury et al. | |
| 5,063,257 A | 11/1991 | Akahane et al. | |
| 5,234,971 A | 8/1993 | Imai et al. | |
| 5,256,065 A * | 10/1993 | Nicholson ................ | A61K 6/40 433/228.1 |
| 5,618,763 A * | 4/1997 | Frank ....................... | A61K 6/16 501/5 |
| 5,891,233 A | 4/1999 | Salonen et al. | |
| 6,217,644 B1 | 4/2001 | Matsunae et al. | |
| 6,353,039 B1 | 3/2002 | Rheinberger et al. | |
| 10,646,408 B2 * | 5/2020 | Yoshimitsu ............. | C03C 12/00 |
| 10,646,410 B2 * | 5/2020 | Yoshimitsu ............. | C03C 3/112 |
| 10,806,680 B2 * | 10/2020 | Honda .................... | A61K 6/887 |
| 2002/0035025 A1 | 3/2002 | Schweiger et al. | |
| 2004/0234462 A1 | 11/2004 | Algar et al. | |
| 2007/0129459 A1 | 6/2007 | Zeng et al. | |
| 2009/0131551 A1 | 5/2009 | Xie | |
| 2009/0208428 A1 | 8/2009 | Hill et al. | |
| 2010/0311864 A1 | 12/2010 | Arita et al. | |
| 2011/0009511 A1 | 1/2011 | Hill et al. | |
| 2011/0045052 A1 * | 2/2011 | Hill ....................... | C03C 4/0007 424/423 |
| 2012/0135059 A1 | 5/2012 | Tsunekawa et al. | |
| 2014/0056954 A1 | 2/2014 | O'Donnell et al. | |
| 2016/0193118 A1 * | 7/2016 | Hatanaka ............... | A61Q 11/00 424/489 |
| 2017/0105906 A1 | 4/2017 | Welch et al. | |
| 2017/0296312 A1 | 10/2017 | Welch et al. | |
| 2019/0083364 A1 | 3/2019 | Yoshimitsu et al. | |
| 2019/0099332 A1 | 4/2019 | Yoshimitsu et al. | |
| 2019/0142702 A1 | 5/2019 | Honda et al. | |
| 2019/0151204 A1 | 5/2019 | Akiyama et al. | |

FOREIGN PATENT DOCUMENTS

| | | |
|---|---|---|
| EP | 2462914 | 6/2012 |
| JP | S62-067008 | 3/1987 |
| JP | S63-201038 | 8/1988 |

(Continued)

OTHER PUBLICATIONS

Z Abbasi, ME Bahrololoom, MH Shariat, R Bagheri. "Bioactive Glasses in Dentistry: A Review." Journal of Dental Biomaterials, vol. 2(1), 2015, pp. 1-9. (Year: 2015).*

L Malcmacher. "To Etch or Not to Etch." https://www.dentaleconomics.com/science-tech/composite-resin-materials/article/16387689/to-etch-or-not-to-etch accessed Apr. 6, 2020, published Jul. 1, 2003, pp. 1-9. (Year: 2003).*

Natasha Madan, Neeraj Madan, Vikram Sharma, Deepak Pardal, and Nidhi Madan. "Tooth remineralization using bio-active glass—A novel approach." Journal of Academy of Advanced Dental Research, vol. 2; Issue 2: May 2011, pp. 45-50. (Year: 2011).*

Dong-Ae Kim, Hany A. Abo-Mosallam, Hye-Young Lee, Gyu-Ri Kim, Hae-Won Kim, Hae-Hyoung Lee. "Development of a novel aluminum-free glass ionomer cement based on magnesium/strontium-silicate glasses." Materials Science and Engineering C 42 (2014) 665-671. (Year: 2014).*

Filipa O. Gomes, Ricardo A. Pires and Rui L. Reis. "Aluminum-free glass-ionomer bone cements with enhanced bioactivity and biodegradability." Materials Science and Engineering C, vol. 33, (2013), pp. 1361-1370. (Year: 2013).*

(Continued)

*Primary Examiner* — Isaac Shomer
(74) *Attorney, Agent, or Firm* — IPUSA, PLLC

(57) ABSTRACT

A dental treatment material includes: a liquid dispersion of a glass powder; and an inorganic phosphoric acid aqueous solution, wherein the glass powder contains zinc, silicon, and fluorine and does not substantially contain aluminum.

6 Claims, No Drawings

(56) References Cited

FOREIGN PATENT DOCUMENTS

| | | | | |
|---|---|---|---|---|
| JP | H04-217904 | 8/1992 | | |
| JP | H09-249515 | 9/1997 | | |
| JP | H10-506908 | 7/1998 | | |
| JP | H11-268929 | 10/1999 | | |
| JP | 2000-026225 | 1/2000 | | |
| JP | 2000-086421 | 3/2000 | | |
| JP | 2001-130926 | 5/2001 | | |
| JP | 2002-053339 | 2/2002 | | |
| JP | 2003-507302 | 2/2003 | | |
| JP | 2009-539755 | 11/2009 | | |
| JP | 2010-532338 | 10/2010 | | |
| JP | 2010-280630 | 12/2010 | | |
| JP | 2012-531377 | 12/2012 | | |
| WO | 90/015782 | 12/1990 | | |
| WO | WO-9015782 A1 * | 12/1990 | ............... | C03C 8/14 |
| WO | 2005/074862 | 8/2005 | | |
| WO | 2007/144662 | 12/2007 | | |
| WO | WO-2007144662 A1 * | 12/2007 | ............. | C03C 3/112 |
| WO | 2011/016395 | 2/2011 | | |

OTHER PUBLICATIONS

International Search Report for PCT/JP2017/020896 dated Aug. 8, 2017.
International Search Report for PCT/JP2017/016611 dated Jun. 13, 2017.
International Search Report for PCT/JP2016/085805 dated Jan. 17, 2017.
International Search Report for PCT/JP2016/085806 dated Jan. 17, 2017.
U.S. Office Action for U.S. Appl. No. 16/086,801 dated Jan. 27, 2020.
U.S. Office Action for U.S. Appl. No. 16/306,968 dated Feb. 21, 2020.
Smith D.C. "Medical and Dental Applications of Cements", 1971, J. Biomed. Mater. Res. Symposium, John Wiley & Sons, Inc., vol. 1, pp. 189-205. (Year: 1971).

* cited by examiner

DENTAL TREATMENT MATERIAL AND DENTAL TREATMENT MATERIAL KIT

TECHNICAL FIELD

The present invention relates to a dental Treatment material and a dental treatment material kit.

BACKGROUND ART

Conventionally, in dental treatment, a dental treatment material that is applied to an affected part for alleviating symptoms of hyperesthesia or the like is known. In particular, a treatment material that seals dentinal tubules of dentine exposed at an affected part to block external stimuli to alleviate pain is well known.

For example, Patent Document 1 describes a dental treatment material containing two liquids that promptly causes precipitation hardly soluble in water when being mixed.

PRIOR ART DOCUMENT

Patent Document

[Patent Document 1] Japanese Laid-open Patent Publication No. H4-217904

DISCLOSURE OF THE INVENTION

Problem to be Solved by the Invention

However, conventional dental treatment materials have room for improvement with respect to suppression of tooth demineralization.

Hence, an object in one aspect of the present invention is to provide a dental treatment material having an enhanced effect of suppressing tooth demineralization.

Means for Solving the Problem

According to one aspect of the present invention, a dental treatment material includes: a liquid dispersion of a glass powder; and an inorganic phosphoric acid aqueous solution, wherein the glass powder contains zinc, silicon, and fluorine and does not substantially contain aluminum.

Effects of the Invention

According to one aspect of the present invention, it is possible to provide a dental treatment material having an enhanced effect of suppressing tooth demineralization.

EMBODIMENT FOR CARRYING OUT THE INVENTION

[Dental Treatment Material]

According to one aspect of the present invention, a dental treatment material includes: a liquid dispersion of a glass powder (liquid A); and an inorganic phosphoric acid aqueous solution (liquid B), wherein the glass powder contains zinc, silicon, and fluorine and does not substantially contain aluminum.

Generally, it is known that when a tooth is exposed to an acidic environment for a certain period of time or more, a phenomenon in which a component of the tooth is eluted, that is, tooth demineralization occurs. If this tooth decalcification occurs excessively, dental diseases such as dental caries may occur. Therefore, in the dental care field, there is a demand for dental treatment materials exhibiting an excellent tooth demineralization effect. Then, the inventors of the present invention have conducted earnest studies on a dental treatment material that can enhance the effect of suppressing tooth demineralization. As a result, the inventors of the present invention have found that tooth demineralization can be effectively suppressed by a dental treatment material that includes a liquid dispersion of a glass powder (liquid A); and an inorganic phosphoric acid aqueous solution (liquid B) in which the liquid dispersion of the glass powder (liquid A) includes the glass powder having a specific composition.

The liquid A and the liquid B described above can be mixed for use, and the above described effect can be exhibited by the mixture. In the following, each liquid will be described.

(Liquid Dispersion of Glass Powder (Liquid A))

According to one aspect of the present invention, the glass powder in the liquid A contains zinc, silicon and fluorine and does not substantially contain aluminum.

When the glass powder contains zinc, because the crystals of a tooth can be strengthened and the resistance to acids can be added, tooth demineralization can be effectively suppressed. Also, because an antibacterial effect is added to the dental treatment material, growth of bacteria in a mouth can also be suppressed.

The content of zinc in the glass powder is preferably greater than or equal to 10% by mass and less than or equal to 60% by mass, and is more preferably greater than or equal to 20% by mass and less than or equal to 55% by mass, in terms of zinc oxide (ZnO). When the content of zinc in the glass powder in terms of zinc oxide (ZnO) is greater than or equal to 10% by mass, the effect of suppressing tooth demineralization of the dental treatment material can be enhanced. When the content of zinc in the glass powder in terms of zinc oxide (ZnO) is less than or equal to 60% by mass, because a glass powder having a high transparency is easily obtained, the transparency of the dental treatment material can be enhanced.

Here, silicon serves to form a network in glass.

The content of silicon in the glass powder is preferably greater than or equal to 15% by mass and less than or equal to 50% by mass, and is more preferably greater than or equal to 20% by mass and less than or equal to 40% by mass, in terms of silicon oxide ($SiO_2$). When the content of silicon in the glass powder in terms of silicon oxide ($SiO_2$) is greater than or equal to 15% by mass, a glass powder having a high transparency is easily obtained.

When the glass powder contains fluorine, a tooth can be strengthened. The content of fluorine (F) in the glass powder is preferably greater than or equal to 1% by mass and less than or equal to 30% by mass, and is more preferably greater than or equal to 3% by mass and less than or equal to 20% by mass. When the content of fluorine (F) in the glass powder is greater than or equal to 1% by mass, the effect of reinforcing a tooth can be further enhanced.

Also, when the glass powder does not substantially contain aluminum, tooth demineralization of the dental treatment material can be effectively suppressed. Here, the glass powder not substantially containing aluminum means not intentionally adding (mixing) it as a component and means that the content of aluminum is less than or equal to 1% by mass in terms of aluminum oxide ($Al_2O_3$).

Even when an aluminum compound is not mixed in a material composition for a glass powder, this is in consideration of an aluminum compound mixed as an impurity in a producing process of the glass powder, a detection error of a fluorescent X-ray analyzer for evaluating a composition of the glass powder, and the like. Normally, unless an aluminum compound is mixed in a material for a glass powder, the content of aluminum in the glass powder does not exceed 1% by mass in terms of aluminum oxide ($Al_2O_3$).

The content of aluminum in the glass powder is preferably greater than or equal to 0% by mass and less than or equal to 0.5% by mass, and is more preferably greater than or equal to 0% by mass and less than or equal to 0.3% by mass, in tams of aluminum oxide ($Al_2O_3$).

The glass powder may further contain an optional component. For example, the glass powder may further contain one or more kinds selected from calcium, phosphorus, strontium, lanthanum, sodium, potassium, and the like.

The content of calcium in the glass powder is preferably greater than or equal to 0% by mass and less than or equal to 30% by mass, and is more preferably greater than or equal to 5% by mass and less than or equal to 20% by mass, in terms of calcium oxide (CaO).

The content of phosphorus in the glass powder is preferably greater than or equal to 0% by mass and less than or equal to 10% by mass, and is more preferably greater than or equal to 0% by mass and less than or equal to 5% by mass, in terms of phosphorus oxide (V) ($P_2O_5$).

The content of strontium in the glass powder is preferably greater than or equal to 0% by mass and less than or equal to 40% by mass, and is more preferably greater than or equal to 10% by mass and less than or equal to 30% by mass, in terms of strontium oxide (SrO). When the glass powder contains strontium, the X-ray contrast property when the dental treatment material is applied to a tooth is enhanced.

The content of lanthanum in the glass powder is preferably greater than or equal to 0% by mass and less than or equal to 50% by mass, and is more preferably greater than or equal to 10% by mass and less than or equal to 40% by mass in terms of lanthanum oxide ($La_2O_3$). When the glass powder contains lanthanum, the resistance to acids of the dental treatment material is enhanced.

The content of sodium in the glass powder is preferably greater than or equal to 0% by mass and less than or equal to 15% by mass, and is more preferably greater than or equal to 1% by mass and less than or equal to 10% by mass, in terms of sodium oxide ($Na_2O$). When the glass powder contains sodium, the refractive index of the glass powder is lowered, the glass powder having a high transparency is easily obtained, and the transparency of the dental treatment material can be enhanced.

The content of potassium in the glass powder is preferably greater than or equal to 0% by mass and less than or equal to 10% by mass, and is more preferably greater than or equal to 1% by mass and less than or equal to 5% by mass, in terms of potassium oxide ($K_2O$). When the glass powder contains potassium, the refractive index of the glass powder is lowered, the glass powder having a high transparency is easily obtained, and the transparency of the dental treatment material can be enhanced.

A glass powder can be produced by melting a material composition, in which materials corresponding to the respective components described above are mixed, to be homogeneous and thereafter cooling and pulverizing the material composition.

Examples of a material corresponding to zinc include, but are not limited to, zinc oxide, zinc fluoride, and the like, and two or more kinds may be used in combination as the material.

Examples of a material corresponding to silicon include, but are not limited to, anhydrous silicic acid and the like, and two or more kinds may be used in combination as the material.

Examples of a material corresponding to fluorine include, but are not limited to, calcium fluoride, strontium fluoride, sodium fluoride, and the like, and two or more kinds may be used in combination as the material.

Examples of a material corresponding to calcium include, but are not limited to, calcium fluoride, calcium phosphate, calcium carbonate, calcium hydroxide and the like, and two or more kinds may be used in combination as the material.

Examples of a material corresponding to phosphorus include, but are not limited to, calcium phosphate, strontium phosphate, sodium dihydrogenphosphate, diphosphorus pentoxide, and the like, and two or more kinds may be used in combination as the material.

Examples of a material corresponding to strontium include, but are not limited to, strontium fluoride, strontium hydroxide, strontium carbonate, strontium oxide, strontium phosphate, and the like, and two or more kinds may be used in combination as the material.

Examples of a material corresponding to lanthanum include, but are not limited to, lanthanum fluoride, lanthanum oxide, and the like, and two or more kinds may be used in combination as the material.

Examples of a material corresponding to sodium include, but are not limited to, sodium dihydrogenphosphate, sodium carbonate, sodium fluoride, and the like, and two or more kinds may be used in combination as the material.

Examples of a material corresponding to potassium include, but are not limited to, potassium fluoride, potassium carbonate, potassium hydrogencarbonate, dipotassium hydrogen phosphate, and the like, and two or more kinds may be used in combination as the material.

The number average particle diameter of particles of a glass powder according to one aspect of the present invention is preferably less than or equal to 1 μm, is more preferably greater than or equal to 0.02 μm and less than or equal to 1 μm, and is further more preferably greater than or equal to 0.1 μm and less than or equal to 0.5 μm. When the number average particle diameter of glass powder particles of is greater than or equal to 0.02 μm, a glass powder in a good dispersion state can be obtained. When the number average particle diameter is less than or equal to 1 μm, the dental treatment material can be certainly applied to a tooth surface that is an affected part (an assured tooth application property can be obtained), and elongated tubules or holes such as dentinal tubules can be favorably sealed.

Note that the number average particle diameter refers to a median diameter measured by a laser diffraction scattering type particle size distribution meter.

In a dental treatment material according to one embodiment of the present invention, the above described glass powder is used in a configuration of being dispersed in a dispersion medium. The content of the glass powder in the liquid dispersion (liquid A), that is, the concentration of the liquid A is preferably greater than or equal to 1% by mass and less than or equal to and 50% by mass, and is more preferably greater than or equal to 5% by mass and less than or equal to 50% by mass. When the concentration of the glass powder in the liquid dispersion medium is greater than or equal to 1% by mass, it is possible to enhance the effect of suppressing tooth demineralization and to exert an assured application property to a tooth surface. Also, when the concentration of the glass powder in the liquid dispersion medium is less than or equal to 50% by mass, it is possible to secure a good viscosity for use, and it is possible to enhance operability.

The dispersion medium is not particularly limited as long as it disperses a glass powder well and does not prevent a reaction between the glass powder and an inorganic phosphoric acid in the liquid B. As the dispersion medium, water, an aqueous solution, an organic solvent or the like is used and water is preferable. When water is used as the dispersion medium, two or more kinds of water-soluble other media can be used in combination.

Also, the liquid dispersion of the glass powder (liquid A) may further contain an additive such as a preservative, an antibacterial agent, a dispersing aid, a pH adjusting agent, and a pigment.

(Inorganic Phosphoric Acid Aqueous Solution (Liquid B))

An inorganic phosphoric acid aqueous solution (liquid B) according to one aspect of the present invention can be obtained by dissolving or diluting one of phosphoric acid, pyrophosphoric acid, tripolyphosphoric acid, metaphosphoric acid, polyphosphoric acid, and the like or a combination including two or more these acids with water. An inorganic phosphoric acid aqueous solution is preferably prepared by diluting concentrated phosphoric acid with distilled water. Also, additionally or singly, potassium hydrogen phosphate, potassium dihydrogen phosphate, calcium phosphate, monopotassium phosphate, sodium metaphosphate, monosodium phosphate, potassium orthophosphate, sodium orthophosphate, ammonium orthophosphate, and calcium orthophosphate, and a combination of these may be used.

The content of the inorganic phosphoric acid in the inorganic phosphoric acid aqueous solution (liquid B), that is, the concentration of the liquid B is preferably greater than or equal to 0.5% by mass and less than or equal to 40% by mass, and is more preferably greater than or equal to 1% by mass and less than or equal to 30% by mass. By making the concentration of the inorganic phosphoric acid greater than or equal to 0.5% by mass, an excellent effect of suppressing tooth demineralization can be obtained when being mixed with the liquid A. Also, by making the concentration less than or equal to 40% by mass, a tooth can be prevented from being excessively demineralized.

The inorganic phosphoric acid aqueous solution (liquid B) may further contain an additive such as a preservative, an antimicrobial agent, a dispersing aid, a pH adjusting agent, or a pigment.

A dental treatment material according to the present embodiment includes the liquid A and the liquid B described above, and these liquids can be mixed for use. In this case, the value of the ratio of the mass of the liquid dispersion of the glass powder (liquid A) to the mass of the inorganic phosphoric acid aqueous solution (liquid B) (mass of liquid A/mass of liquid B) is preferably greater than or equal to 0.4 and less than or equal to 2.5, and is more preferably greater than or equal to 0.5 and less than or equal to 2.0. When it is in the above described range, the effect of suppressing tooth demineralization can be further enhanced. When it is greater than or equal to 0.4, it is possible to secure an assured application property to a tooth surface, and when it is less than or equal to 2.5, it is possible to secure a good viscosity for use, and to prevent excessive demineralization of a tooth.

According to the dental treatment material according to one aspect of the present invention, when the glass powder in the liquid A and the inorganic phosphoric acid in the liquid B are mixed, an aggregate (precipitate) is generated. This aggregate works to seal tubules, pores, scratches, and the like of a tooth. Therefore, the dental treatment material according to one aspect of the present invention can be suitably used as a dentinal tubules sealing material, and can be particularly preferably used as a hyperesthesia suppressing material. Other than a hyperesthesia suppressing material, the dental treatment material according to one aspect of the present invention can also be used as a primer for application to an affected part before performing a coating treatment or a filling treatment, as a root canal filling material for sealing a root canal and/or an apical foramen, or the like.

Note that the dental treatment material may be in a configuration containing a mixture of a liquid dispersion of a glass powder (liquid A) and an inorganic phosphoric acid aqueous solution (liquid B), or may be in a configuration in which a liquid dispersion of a glass powder (liquid A) and an inorganic phosphoric acid aqueous solution (liquid B) are separate from each other so as not to be mixed. In the latter case, the dental treatment material may be in a configuration in which the respective liquids are contained in different containers. Also, the dental treatment material may be in a configuration of being contained in a container within which a film, a wall, or the like is provided such that the film, the wall, or the like separates the liquids to prevent the liquids from being directly in contact with each other. In a case of being contained in a container within which a film, a wall, or the like is provided, the liquids can be mixed at the time of use by removing the film, the wall, or the like or by extracting the respective liquids without removing the film, the wall, or the like.

In any configuration described above, the dental treatment material of one aspect of the present invention can be used only by mixing components of the liquid A and components of the liquid B, and has an operability higher than that of a conventional dental treatment material that requires a hardening process by light or heat. Also, a process such as kneading is unnecessary in use.

Dental Treatment Material Kit

According to one aspect of the present invention, it is possible to provide a dental treatment material kit including: a container in which the liquid dispersion of the glass powder (liquid A) that contains zinc, silicon, and fluorine and does not substantially contain aluminum is contained; and a container in which the inorganic phosphoric acid aqueous solution (liquid B) is contained.

Immediately before using the dental treatment material kit, the liquid dispersion of the glass powder (liquid A) is extracted from the container, in which the liquid dispersion of the glass powder is contained, and the inorganic phosphoric acid aqueous solution (liquid B) is extracted from the container, in which the inorganic phosphoric acid aqueous solution is contained. Then, these extracted liquids are mixed and the mixed liquid can be applied to an affected part for use. Also, by applying the liquid A and the liquid B to an affected part in any sequential order, these liquids can be mixed at the affected part.

At the time of application, an applicator having a brush, a cotton-like material, a porous material or the like provided at its tip can be used. Because the liquid dispersion of the glass powder (liquid A) and the inorganic phosphoric acid aqueous solution (liquid B) are in a liquid state or slurry state, a mixing operation is easy. Further, an application to an affected part is easy.

Note that although the containers for containing the respective liquids of a dental treatment material kit are not particularly limited, containers that can protect the respective liquids from being affected by an external environment such as light without modifying the liquids that are contained are preferable, for example.

EXAMPLES

In the following; the present invention will be described in detail with reference to Examples and Comparative Examples. Note that the present invention is not limited to the examples.

Examples 1 to 12

(1) Preparation of Glass Powder

After zinc oxide (ZnO), anhydrous silicic acid ($SiO_2$), calcium fluoride ($CaF_2$), calcium phosphate ($Ca_3(PO_4)_2$), strontium fluoride ($SrF_2$), phosphorus oxide ($P_2O_5$), lanthanum oxide ($La_2O_3$), sodium fluoride (NaF), and potassium hydrogen carbonate ($KHCO_3$) were mixed at a predetermined ratio, and the mixture was sufficiently mixed and stirred using a mortar. The material composition, which is the obtained mixture, was placed in a platinum crucible, and it was placed in an electric furnace. The electric furnace was heated to 1300° C., and the mixture was melted and sufficiently homogenized. Subsequently, the mixture was poured into water to obtain aggregated glass. Using a ball mill made of alumina, the obtained aggregated glass was crushed for 20 hours, then it was caused to pass through a sieve of 120 meshes, and it was wet-crushed for 70 hours to obtain a glass powder.

The particle diameters and the compositions of the obtained glass powders were measured by the following methods.

<Composition of Glass Powder>

Using a fluorescent X-ray analyzer ZSX Primus II (manufactured by Rigaku Corporation), the glass powders were analyzed to find their compositions.

Table 1 indicates the compositions of the glass powders (unit: mass %). Note that the contents of Zn, Al, Si, Ca, P, Sr, La, Na, and K, which are components other than F, are respectively in mass % in terms of ZnO, $Al_2O_3$, $SiO_2$, CaO, $P_2O_5$, SrO, $La_2O_3$, $Na_2O$, and $K_2O$.

Note that although an aluminum compound was not mixed in the material composition in each of Examples 1 to 12, 0.1% by mass or more and 0.5% or less by mass of aluminum was detected in terms of aluminum oxide ($Al_2O_3$) with respect to the total amount of the glass powder. A possible cause of this is that alumina derived from a ball made of alumina or a pot made of alumina used at the time of crush was mixed or a detection error of a fluorescent X-ray analyzer.

<Particle Diameter of Glass Powder>

The particle size distributions of the glass powders were measured using a laser diffraction scattering type particle size distribution analyzer LA-950 (manufactured by HORIBA, Ltd.) Table 1 indicates the number average particle diameters (median diameters) of the respective glass powders used for Examples and Comparative Examples.

(2) Preparation of Liquid Dispersion of Glass Powder (Liquid A)

Each glass powder obtained above was dispersed in distilled water to obtain a liquid dispersion of a glass powder (liquid A) having the concentration indicated in Table 1.

(3) Preparation of Inorganic Phosphoric Acid Aqueous Solution (Liquid B)

Concentrated phosphoric acid was diluted with distilled water to prepare aqueous solutions of inorganic phosphoric acid, and inorganic phosphoric acid aqueous solutions (liquid B) each of which has the concentration indicated in Table 1 were obtained.

Comparative Examples 1 to 6

(1) Preparation of Glass Powder

After zinc oxide (ZnO), aluminum oxide ($Al_2O_3$), aluminum fluoride ($AlF_3$), anhydrous silicic acid ($SiO_2$), calcium fluoride ($CaF_2$), calcium phosphate ($Ca_3(PO_4)_2$), strontium fluoride ($SrF_2$), phosphorus oxide ($P_2O_5$), lanthanum oxide ($La_2O_3$), sodium fluoride (NaF), and potassium hydrogen carbonate ($KHCO_3$) were mixed at a predetermined ratio, and the mixture was sufficiently mixed and stirred using a mortar. The material composition, which is the obtained mixture, was placed in a platinum crucible, and it was placed in an electric furnace. The electric furnace was heated to 1300° C., and the mixture was melted and sufficiently homogenized. Subsequently, the mixture was poured into water to obtain aggregated glass. Using a ball mill made of alumina, the obtained aggregated glass was crushed for 20 hours, then it was caused to pass through a sieve of 120 meshes, and it was wet-crushed for 70 hours to obtain a glass powder.

Next, the particle diameters and the compositions of the glass powders were measured by methods similar to those performed for the glass powders of Examples 1 to 12. The Results are Indicated in Table 1.

(2) Preparation of Liquid Dispersion of Glass Powder (Liquid A)

Each glass powder obtained above was dispersed in distilled water to obtain a liquid dispersion of a glass powder (liquid A) having the concentration indicated in Table 1.

(3) Preparation of Inorganic Phosphoric Acid Aqueous Solution (Liquid B)

Concentrated phosphoric acid was diluted with distilled water to prepare aqueous solutions of inorganic phosphoric acid, and inorganic phosphoric acid aqueous solutions (liquid B) each of which has the concentration indicated in Table 1 were obtained.

For each of the dental treatment materials of Examples and Comparative Examples described above, the dentinal tubules sealing property and the effect of suppressing tooth demineralization were evaluated.

<Evaluation of Property of Sealing Dentinal Tubules>

While water was poured, bovine dentine was polished by #1200 water-resistant abrasive paper. The flat polished surface was processed with a 15% aqueous solution of EDTA for one minute to obtain simulated hyperesthesia dentine. For each of Examples and Comparative Examples, the liquid A and the liquid B were extracted at the mass ratio indicated in Table 1, and mixed using an applicator to obtain a mixed liquid (dental treatment material). Each mixed liquid was applied to the simulated hyperesthesia dentine. After leaving it for 20 seconds, it was washed with water, dried, and observed with a scanning electron microscope (SEM) to check the dentinal tubules sealing property. Evaluation criteria are as follows.

GOOD: When it was observed that all or almost all of dentinal tubules were sealed POOR: When unsealed dentinal tubules were visible <Evaluation of Effect of Suppressing Tooth Demineralization>

While water was poured, bovine dentine was polished by #1200 water-resistant abrasive paper. To the flat polished surface, a polytetrafluoroethylene seal, having a hole of which diameter is 3 mm, was attached. Liquid A and Liquid B obtained for each of Examples and Comparative Examples were extracted at the mass ratio indicated in Table 1 and mixed using an applicator to obtain a mixed liquid (dental treatment material). Each mixed liquid was applied to the surface, to which the seal was attached, to cover the entire hole of the seal. It was left to stand for 20 seconds, and subsequently, it was washed with water, and dried. Thereafter, it was immersed in a demineralized liquid (50 mM of acetic acid, 1.5 mM of calcium chloride, 0.9 mM of potassium dihydrogen phosphate, pH 4.5) at 37° C. for 18 hours.

Using a precision cutting machine, the bovine dentin, on which a hardened layer was formed, was cut such that the thickness became 1 mm, and a test object was obtained.

Using an X-ray inspection apparatus, the test object was photographed by a transmission method. Using image processing software, the photographed image was analyzed to find the amount of mineral loss and to evaluate the effect of suppressing tooth demineralization. The criteria for determining the effects of suppressing tooth demineralization are as follows. Note that as the value of the amount of mineral loss decreases, the effect of suppressing tooth demineralization increases.

GOOD: When the amount of mineral loss is less than 2500 volume %·μm

Poor: When the amount of mineral loss is greater than or equal to 2500 volume %·μm Comparative Example 7

Except that a dental treatment material is not applied to a tooth at all, the dentinal tubules sealing property and the effect of suppressing tooth demineralization were evaluated in a manner similar to that described above. The results are indicated in Table 1.

TABLE 1

| | | Example | | | | | | | | | |
|---|---|---|---|---|---|---|---|---|---|---|---|
| | | 1 | 2 | 3 | 4 | 5 | 6 | 7 | 8 | 9 | 10 |
| *COMPOSITION OF GLASS POWDER OF LIQUID A (MASS %) | Zn | 50.5 | 30.0 | 26.4 | 23.8 | 45.0 | 49.5 | 41.7 | 25.2 | 26.4 | 26.4 |
| | F | 3.0 | 5.2 | 6.5 | 6.8 | 3.3 | 3.2 | 4.7 | 5.8 | 6.5 | 6.5 |
| | Al | 0.3 | 0.3 | 0.3 | 0.5 | 0.3 | 0.1 | 0.3 | 0.2 | 0.3 | 0.3 |
| | Si | 33.0 | 22.9 | 24.7 | 23.1 | 35.5 | 34.8 | 37.7 | 26.8 | 24.7 | 24.7 |
| | Ca | 13.2 | 7.1 | 9.6 | 9.3 | 11.4 | — | 12.1 | 6.6 | 9.6 | 9.6 |
| | P | — | — | — | — | 4.5 | — | — | — | — | — |
| | Sr | — | — | — | — | — | 12.4 | — | — | — | — |
| | La | — | 34.5 | 32.5 | 36.5 | — | — | — | 33.2 | 32.5 | 32.5 |
| | Na | — | — | — | — | — | — | 3.5 | — | — | — |
| | K | — | — | — | — | — | — | — | 2.2 | — | — |
| TOTAL | | 100 | 100 | 100 | 100 | 100 | 100 | 100 | 100 | 100 | 100 |
| LIQUID A CONCENTRATION | | 30% | 30% | 30% | 30% | 30% | 30% | 30% | 30% | 20% | 40% |
| LIQUID B CONCENTRATION | | 5% | 5% | 5% | 5% | 5% | 5% | 5% | 5% | 3% | 10% |
| LIQUID A/LIQUID B MASS RATIO | | 1.0 | 1.0 | 1.0 | 1.0 | 1.0 | 1.0 | 1.0 | 1.0 | 1.0 | 1.0 |
| MEDIAN DIAMETER OF GLASS POWDER [μm] | | 0.4 | 0.3 | 0.4 | 0.3 | 0.5 | 0.4 | 0.3 | 0.5 | 0.5 | 0.5 |
| EVALUATION | AMOUNT OF MINERAL LOSS [VOLUME %·μm] | 2035 | 2235 | 2324 | 2445 | 2001 | 1984 | 2289 | 2310 | 2111 | 1876 |
| | EFFECT OF SUPPRESSING TOOTH DEMINERALIZATION | GOOD | GOOD | GOOD | GOOD | GOOD | GOOD | GOOD | GOOD | GOOD | GOOD |
| | DENTINAL TUBULES SEALING PROPERTY | GOOD | GOOD | GOOD | GOOD | GOOD | GOOD | GOOD | GOOD | GOOD | GOOD |

| | | Example | | Comparative Example | | | | | | |
|---|---|---|---|---|---|---|---|---|---|---|
| | | 11 | 12 | 1 | 2 | 3 | 4 | 5 | 6 | 7 |
| *COMPOSITION OF GLASS POWDER OF LIQUID A (MASS %) | Zn | 26.4 | 26.4 | — | — | — | 4.6 | — | — | — |
| | F | 6.5 | 6.5 | 13.5 | 13.1 | 12.0 | 11.2 | 9.4 | 13.2 | — |
| | Al | 0.3 | 0.3 | 25.9 | 23.9 | 25.9 | 21.3 | 21.4 | 25.5 | — |
| | Si | 24.7 | 24.7 | 23.8 | 24.0 | 25.1 | 23.6 | 20.9 | 23.3 | — |
| | Ca | 9.6 | 9.6 | — | 0.3 | 0.1 | 1.8 | — | — | — |
| | P | — | — | 1.3 | 4.6 | 3.5 | 3.5 | 1.0 | 4.4 | — |
| | Sr | — | — | 35.5 | 34.1 | 31.9 | 28.0 | 47.3 | 21.5 | — |
| | La | 32.5 | 32.5 | — | — | — | 6.0 | — | 4.6 | — |
| | Na | — | — | — | — | 1.5 | — | — | 3.2 | — |
| | K | — | — | — | — | — | — | — | 4.3 | — |
| TOTAL | | 100 | 100 | 100 | 100 | 100 | 100 | 100 | 100 | — |
| LIQUID A CONCENTRATION | | 20% | 30% | 30% | 30% | 30% | 30% | 30% | 30% | — |
| LIQUID B CONCENTRATION | | 5% | 5% | 5% | 5% | 5% | 5% | 5% | 5% | — |
| LIQUID A/LIQUID B MASS RATIO | | 2.0 | 0.5 | 1.0 | 1.0 | 1.0 | 1.0 | 1.0 | 1.0 | — |
| MEDIAN DIAMETER OF GLASS POWDER [μm] | | 0.5 | 0.5 | 0.3 | 0.3 | 0.4 | 0.5 | 0.4 | 0.4 | — |
| EVALUATION | AMOUNT OF MINERAL LOSS [VOLUME %·μm] | 2322 | 2391 | 2816 | 2920 | 2817 | 2611 | 2964 | 2790 | 3781 |

TABLE 1-continued

| | | | | | | | | | |
|---|---|---|---|---|---|---|---|---|---|
| EFFECT OF SUPPRESSING TOOTH DEMINERALIZATION | GOOD | GOOD | POOR | POOR | POOR | POOR | POOR | POOR | POOR |
| DENTINAL TUBULES SEALING PROPERTY | GOOD | GOOD | GOOD | GOOD | GOOD | GOOD | GOOD | GOOD | POOR |

*COMPOSITIONS OTHER THAN F OF GLASS POWDERS ARE IN MASS % IN TERMS OF OXIDES

As indicated by Table 1, it could be confirmed that the dental treatment materials of Examples 1 to 12 using glass powders, which contain zinc, silicon, and fluorine and do not substantially contain aluminum, have high effects of suppressing tooth demineralization. Conversely, it could be found that the dental treatment materials of Comparative Examples 1 to 3, 5, and 6 using glass powders, which contain aluminum and does not contain zinc, and the dental treatment material of Comparative Examples 4, which contains a small amount of zinc and contains aluminum, have low effects of suppressing tooth demineralization.

Note that among Examples 1 to 12 for which the determination of the effect of suppressing tooth demineralization was "GOOD", it could be confirmed that Example 6, in which the content of aluminum was low and 0.1% by mass in terms of aluminum oxide ($Al_2O_3$), has a particularly low mineral loss amount and a high effect of suppressing tooth demineralization. Further, when the examples containing glass powder having the same composition are compared, Example 10, in which both the liquid A concentration and the liquid B concentration are high, has a low amount of mineral loss and a high effect of suppressing tooth demineralization in comparison with Examples 3, 9, 11, and 12. It could be also confirmed that each of Examples 1 to 12 has a high dentinal tubules sealing property and a high function of sealing dentinal tubules.

The present international application is based on and claims priority to Japanese Patent Application No. 2016-131018, filed on Jun. 30, 2016, the entire contents of which are hereby incorporated herein by reference.

The invention claimed is:

1. A dental treatment material comprising:
a liquid dispersion of a glass powder; and
an inorganic phosphoric acid aqueous solution,
wherein the glass powder contains zinc, silicon, and fluorine and does not substantially contain aluminum, and
wherein a content of zinc oxide (ZnO) in the glass powder is greater than or equal to 20% by mass.

2. The dental treatment material according to claim 1, wherein the dental treatment material is a dentinal tubules sealing material.

3. The dental treatment material according to claim 1, wherein the content of zinc oxide (ZnO) in the glass powder is less than or equal to 60% by mass.

4. The dental treatment material according to claim 1, wherein the content of zinc oxide (ZnO) in the glass powder is less than or equal to 55% by mass.

5. The dental treatment material according to claim 1, wherein the content of zinc oxide (ZnO) in the glass powder is greater than or equal to 23.8% by mass and less than or equal to 50.5% by mass.

6. A dental treatment material kit comprising:
a container in which a liquid dispersion of a glass powder that contains zinc, silicon, and fluorine and does not substantially contain aluminum is contained; and
a container in which an inorganic phosphoric acid aqueous solution is contained,
wherein a content of zinc oxide (ZnO) in the glass powder is greater than or equal to 20% by mass.

* * * * *